United States Patent [19]

Goettsche et al.

[11] Patent Number: 5,186,947
[45] Date of Patent: Feb. 16, 1993

[54] WOOD PRESERVATIVE BASED ON POLYMERIC NITROGEN COMPOUNDS AND METAL-FIXING ACIDS

[75] Inventors: Reimer Goettsche, Baden-Baden; Wolfgang Reuther, Heidelberg, both of Fed. Rep. of Germany

[73] Assignee: Dr. Wolman GmbH, Sinzheim, Fed. Rep. of Germany

[21] Appl. No.: 762,369

[22] Filed: Sep. 19, 1991

[30] Foreign Application Priority Data

Oct. 20, 1990 [DE] Fed. Rep. of Germany ....... 4033419

[51] Int. Cl.$^5$ ................... A01N 59/20; A01N 59/16; A01N 59/26
[52] U.S. Cl. .................. 424/638; 424/605; 424/606; 424/630; 424/632; 424/633; 424/634; 424/635; 424/637; 424/641; 424/659; 424/660; 514/75; 514/134; 514/139; 514/231.2; 514/239.5; 514/372; 514/383; 514/384; 514/396; 514/493; 514/494; 514/499; 514/500; 514/575; 514/642; 514/645; 514/663; 514/673; 514/674
[58] Field of Search ............... 424/630, 633, 634, 638, 424/605, 606, 632, 635, 637, 641, 659, 660; 514/500, 75, 134, 139, 231.2, 239.5, 372, 383, 384, 396, 493, 494, 499, 500, 575, 642, 645, 663, 673, 674

[56] References Cited

U.S. PATENT DOCUMENTS

| | | | |
|---|---|---|---|
| 3,046,188 | 7/1962 | Gaudian et al. | 424/633 |
| 3,769,398 | 10/1973 | Hewitt | 514/556 |
| 4,038,451 | 7/1977 | Brown et al. | 428/274 |
| 4,075,394 | 2/1978 | Meyer | 428/537.1 |
| 4,761,179 | 8/1988 | Goettsche et al. | 424/166 |
| 4,857,322 | 8/1989 | Goettsche et al. | 424/635 |
| 4,871,473 | 10/1989 | Goettsche et al. | 424/640 |

OTHER PUBLICATIONS

The Merck Index, 10th edition, Merck & Co., Inc., Rahway (N.J.), 1983, p. 377.
Chemical Abstracts 103:25453h (1985).

*Primary Examiner*—Allen J. Robinson
*Assistant Examiner*—John D. Pak
*Attorney, Agent, or Firm*—Oblon, Spivak, McClelland, Maier & Neustadt

[57] ABSTRACT

Water-soluble wood preservatives which contain mixtures of a metal compound, a metal-fixing acid and a complexing polymeric nitrogen compound, and methods for protecting wood with such mixtures.

8 Claims, No Drawings

WOOD PRESERVATIVE BASED ON POLYMERIC NITROGEN COMPOUNDS AND METAL-FIXING ACIDS

The present invention relates to water-soluble wood preservatives which comprise a metal compound, a metal-fixing acid and polymeric complexing nitrogen compounds with or without water-soluble amines and/or polyamines.

Water-soluble wood preservatives based on copper and/or zinc compounds, $C_5$–$C_{20}$-carboxylic acids and aliphatic polyamines are known (EP 270 848 and 320 786). Suitable aliphatic polyamines are for example alkylenepolyamines of from 2 to 4 nitrogen atoms. Depending on the nature of the polyamines used, various disadvantages result.

If a polypropylenepolyamine, i.e. for example 1,3-diaminopropane, dipropylenetriamine (3,3,-diaminodipropylamine) or tripropylenetetramine, is applied to solid wood in an industrial process, for example a pressure method, the penetration and distribution of the copper are not always adequate to ensure deep protection of the wood, for example of roundwood such as masts and palisadas, in particular if used in earth contact, i.e. when part of the wood is dug in.

The alkaline aqueous solutions of the copper and/or zinc compounds (pH 8–10 on average) react with the acidic constituents of the wood in such a way that the copper and/or zinc already precipitates in the outer regions of the wood in the presence of carboxylic acids, so that for example in the case of pinewood and if the sapwood thickness is more than 2 cm the copper and/or zinc does not reach the heart of the wood, in particular when the pinewood has narrow annual rings and high resin contents.

Moreover, the copper washout is too high with these wood preservatives, in particular if applied by means of hot steam fixation. For example, more than 20% of the copper present in the wood can be washed out following hot steam fixation (hot steam at about 100° C., 1–2 hours).

With a polyethylene polyamine, e.g. ethylenediamine, diethylenetriamine or triethylenetetramine, aminoethylethanolamine ((2-(2-aminoethyl)amino)ethanol), or 1,2-propanediamine it is true that the penetration is better, but the degree of fixation of the wood preservative is not sufficient with standard or rapid fixation. The copper washout from the wood is for example above 25%.

We have found that the abovementioned disadvantages do not appear in the case of water-soluble wood preservatives based on metal compounds, acids which fix these metals and complexing polymeric nitrogen compounds with or without addition of water-soluble amines and/or polyamines.

Complexing polymeric nitrogen compounds are for example polyethyleneimines, polyamidoamines (condensation products of polyamines with adipic acid), condensation products based for example on diethylenetriamine/triethanolamine and/or diethanolamine/diethylenetriamine. Polyethyleneimines are preferred.

Polyethyleneimines (PEIs) are known and are formed by polymerization of 1,2-ethyleneimine. The nitrogen is present therein in primary form (end group), secondary form and tertiary form (branching). Suitable polyethyleneimines have n greater than 10; very good results are obtained when using PEI having a degree of polymerization n between 50 and 1000.

Polyamidoamines are formed for example by reacting diethylenetriamine with adipic acid at from 150° to 200° C.

Further condensation products are formed for example by heating diethanolamine or triethanolamine to 200°–220° C. in the presence of phosphonic acid ($H_3PO_3$).

Metal compounds are for example copper, zinc, nickel or cobalt compounds or mixtures thereof. They can be used as water-soluble or water-insoluble compounds, for example copper and/or zinc salts such as sulfates, acetates, hydroxides, oxides, borates, fluorides, copper hydroxide carbonate or zinc carbonate; it is also possible to use the corresponding nickel and/or cobalt compounds. Copper compounds are preferred.

Metal-fixing acids are for example aliphatic $C_5$–$C_{20}$-carboxylic acids such as hexanoic acid, heptanoic acid, octanoic acid, branched carboxylic acids, 2-ethylpentanoic acid, 2-ethylhexanoic acid, 2-ethylheptanoic acid, isooctanoic acid, isononanoic acid, more highly branched carboxylic acids such as neocarboxylic acids, Versatic acids, di-n-alkylacetic acids, di-n-alkylpropionic acids, substituted $C_5$–$C_{20}$-carboxylic acids, for example halocarboxylic acids (2-bromohexanoic acid, 2-bromooctanoic acid), ethercarboxylic acids, aminocarboxylic acids, aliphatic dicarboxylic acids, e.g. sebacic acid, cycloalkylcarboxylic acids, e.g. cyclo-hexanecarboxylic acid, cycloarylcarboxylic acids, e.g. phthalic acid, salicylic acid, 3- or 4-hydroxybenzoic acid, aminohydroxycarboxylic acids, e.g. aminosalicylic acid, polycarboxylic acids, e.g. polyacrylic acids and/or other metal-fixing acids such as 2-mercaptopyridine N-oxide, 2-hydroxypyridine N-oxide, dehydroacetic acid, heterocyclic carboxylic acids, e.g. furancarboxylic acid and 2,5-dimethylfurancarboxylic acid.

It is also possible to use the corresponding alkali metal and/or amine and/or copper, zinc, cobalt or nickel salts of the metal-fixing acids.

The copper, zinc, cobalt and nickel salts of the abovementioned acids are water-insoluble; they are converted into water-soluble compounds by the complexing polymeric nitrogen compounds.

For ease of formulation and for economic reasons it is usually advantageous to replace some of the complexing polymeric nitrogen compounds with water-soluble amines and/or polyamines or ammonia. It is possible to use for example aliphatic linear or branched polyamines, e.g. ethylenediamine, diethylenetriamine,, triethylenetetramine, aminoethylethanolamine, 1,2-diaminopropane, 1,3-diaminopropane, dipropylenetriamine, tripropylenetetramine, neopentanediamine, N,N'-bis(3-aminopropyl)ethylenediamine ($N_4$-amine), water-soluble amines, e.g. alkanolamines such as ethanolamine, diethanolamine, triethanolamine or isopropanolamine, polyetherdiamines, e.g. compounds of the formula

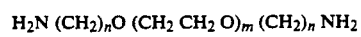

n; m = 1–6 and/or di- or polyamines of cyclic compounds, e.g. 1,3-diaminocyclohexane or N-aminoethylpiperazine.

The amount used of these water-soluble amines must be limited for example by the requirement that neither the penetration of the wood preservative be impaired nor the washout of the metals be increased. Compared to the amines, the polymeric complexing nitrogen compounds are always present in excess.

Since a broad spectrum of activity against wood-destroying animal and vegetable pests is usually only achieved at higher application rates (more than 30 kg of wood preservative per cubic meter of wood), it is for example advantageous to complement and so improve the activity of the wood preservatives of the present invention by the addition of further fungicides or insecticides.

Suitable additives are in particular for example N-organodiazeniumdioxy compounds (HDO compounds) such as N-cyclohexyl-, N-$C_4$-$C_{10}$-alkyl-, in particular, N-$C_6$-$C_8$—alkyl-, N-aryl-, in particular N-phenyl-, -diazeniumdioxy compounds and mixtures thereof. Suitable salts of N-organodiazeniumdioxy compounds are for example not only the water-soluble alkali metal and/or ammonium salts but also the water-insoluble metal salts, such as the copper, zinc, nickel and/or cobalt salts.

An improvement in the activity spectrum against wood-destroying and wood-discoloring fungi and against wood-destroying insects is also possible by mixing in fatty amines (primary, secondary, tertiary amines) which contain at least one hydrophilic moiety of at least 6 carbon atoms.

These amines conform for example to the formula a) $R^1-\underset{\underset{R}{|}}{N}-R^2$  or  b) $R-\underset{\underset{R^1}{|}}{N}-(CH_2)_n-\underset{\underset{R^3}{|}}{N}-R^2$ c) $R-N\underset{\diagdown}{\overset{\diagup}{}}\begin{matrix}(CH_2)_n-NH\\ |\\ R^1\\ \\ (CH_2)_n-NH\\ |\\ R^2\end{matrix}$  n = 1-20 where

R is $C_6$-$C_{20}$-alkyl or -hydroxyalkyl, and $R^1$, and $R^2$ and $R^3$ are each independently of the others hydrogen, $C_1$-$C_4$-alkyl, an R $C_6$-$C_{30}$-alkyl or -hydroxyalkyl, or substituted or unsubstituted benzyl.

The fatty amines may be incorporated into the novel concentrates or solutions in the form of salts according to their properties, for example wholly or partly as salts of carboxylic acids such as acetic acid, propionic acid or 2-ethylhexanoic acid, with or without emulsifiers.

Suitable fatty amines are for example dimethyl ($C_{10}$-$C_{18}$-alkyl)amine, in particular dimethyl-$C_{12}$/$C_{14}$-alkylamine, methyldioctylamine, methyldidecylamine, octyldiethanolamine, didodecyl-1,3-propylenediamine, $C_{13}$/$C_{15}$-alkyltrimethylenediamine, laurylpropylenediamine, N,N-bis-(3-aminopropyl)laurylamine.

It is also possible to include quaternary ammonium compounds or phosphonium compounds.

A quaternary ammonium compound is for example a compound conforming to the formula $R^1R^2R^3R^4N^+Z^-$, where $R^1$ is alkyl of from 8 to 20 carbon atoms, in particular alkyl of from 12 to 20 carbon atoms, or benzyl which may be substituted by $C_1$-$C_{20}$-alkyl or halogen, $R^2$ is $C_1$-$C_6$-alkyl, $C_3$-$C_9$-alkoxyalkyl, polymeric ethylene oxide (EO) or propylene oxide (PO) with EO or PO n=2−50, $R^3$ is $C_1$-$C_6$-alkyl, $C_3$-$C_4$-alkoxy, polymeric ethylene oxide (EO) or propylene oxide (PO) with EO or PO n=2−50, and $R^4$ is $C_1$-$C_{20}$-alkyl, or any two of $R^1$-$R^4$ are combined with the nitrogen atom to form a heterocyclic radical which contains 4 or 5 carbon atoms, 1 or 2 nitrogen atoms and one, two or three double bonds in which the carbon atoms may be substituted by $C_1$-$C_4$-alkyl or halogen and Z is an acid radical, for example halide.

Suitable phosphonium compounds are in particular compounds of the formula $R^1{}_3R^2P^+Y^-$, where $R^1$ is alkyl of from 1 to 6 carbon atoms, hydroxyalkyl of from 1 to 6 carbon atoms or phenyl, $R^2$ is alkyl of from 8 to 18 carbon atoms, and Y is an acid radical, in particular a halide anion.

The radicals $R^1$ and $R^2$ are preferably straight-chain.

The quaternary phosphonium compounds may be present in the novel concentrates alone or as mixtures. Examples of such phosphonium compounds are tri-methyl-n-dodecylphosphonium chloride, triethyl-n-decylphosphonium bromide, tri-n-propyl-n-tetradecyl-phosphonium chloride, trimethylol-n-hexadecylphosphoniumchloride,tri-n-butyl-n-tetradecylphosphonium chloride, tri-n-butyl-n-dodecylphosphonium bromide, tri-n-butyl-n-decylphosphonium chloride, tri-n-butyl-n-hexadecylphosphonium bromide, tri-n-hexyl-n-decyl-phosphoniun chloride, triphenyl-n-dodecylphos-phonium chloride, triphenyl-n-tetradecylphosphonium bromide and triphenyln-octadecylphosphonium chloride.

It is also possible to add further fungicides, for example in emulsified form, such as N-tridecyl-2,6-dimethylmorpholine (tridemorph) and/or 4-(3-para-tertbutyl-phenyl)-2-methylpropyl-2,6-cis-dimethylmorpholine (fenpropimorph) and/or triazole and/or imidazole compounds such as 1-(2-(2,4-dichlorophenyl)-4-methyl-1,3-dioxolan 2-ylmethyl)-1H-1,2,4-triazole, 1-(2-(2,4-dichlorophenyl)-1,3-dioxolan-2-ylmethyl)-1H-1,2,4-triazole, 1-(2-(2,4-dichlorophenyl)-4-ethyl-1,3-dioxolan-2-yl-methyl)-1H-1,2,4-triazole, 1-(2-(2,4-dichloro-phenyl)-4-propyl-1,3-dioxolan-2-ylmethyl)-1H-1,2,4-triazole (propiconazole), 1-(2-(2,4-dichlorophenyl)-4-pentyl-1,3-dioxolan-2-ylmethyl)-1H-1,2,4-triazole, 1-(2-(2,4-dichlorophenyl)4-ethyl-1,3-dioxolan-2-ylmethyl)-1H-imidazole, α-tert-butyl-α-(p-chlorophenylethyl)-1H-1,2,4-triazol-1-ethanol, 1-(β-alkyloxy-2,4-dichloro-phenethyl)imidazole and/or organotin compounds, in particular tributyltin (TBT) compounds, such as TBT oxide, TBT versatate, TBT benzoate, TBT naphthenate, TBT-HDO and/or isothiazolinone compounds of the following formula:

$\underset{R^3}{\overset{R^2}{}}\diagdown\!\!\!\diagup\!\!\!\underset{S}{\diagdown}\!\!\!\underset{N}{\diagup}\!\!\!\diagdown_{R^1}^{\!\!\!=O}$ where $R^1$ is hydrogen, alkyl, alkenyl or alkynyl of from 1 to 18 carbon atoms, cycloalkyl having a $C_3$-$C_6$-ring and up to 12 carbon atoms, or aralkyl or aryl of up to 19 carbon atoms, and $R^2$ and $R^3$ are each independently of the other hydrogen, halogen or $C_1$–$C_4$-alkyl, or $R^2$ and $R^3$ are part of an aromatic radical, and/or hydroxamic acids of the formula

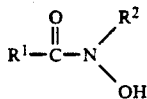

where $R^1$ is for example cycloalkyl (cyclohexyl), aryl (phenyl) or heterocyclyl, and $R^2$ is for example hydrogen, $C_1$–$C_4$-alkyl, $C_5$–$C_8$-cycloalkyl or aryl (phenyl).

Emulsifiers used with or without polar solvents can be in particular the aforementioned fatty amines and their salts, quaternary ammonium/phosphonium compounds and for example other ionic and nonionic emulsifiers.

The wood preservatives may contain further compounds, for example compounds with a fungicidal anion, for example a boron compound, e.g. an alkali metal borate, amine borate, boric acid, boric ester; fluorides, e.g. potassium fluoride, and/or salts of fluoroboric acid and/or fluorophosphoric acid and/or difluorophosphoric acid.

The degree of penetration of aqueous solutions of the novel wood preservatives, for example by pressure impregnation, is very good: the solutions penetrate deep into the wood. The distribution of active substance in the wood conforms to practical requirements. In the impregnation of roundwood, the outer limit of the heart wood is reached even in the case of wide sapwood. Precipitation of the metal salts does not start until after the impregnation, and they are fixed (absorbed) in the wood fibers and constituents with the aid of the polymeric nitrogen compounds.

At about 20° C. the fixation of the wood preservative of the present invention is for example complete after 1 to 2 weeks; the fixation reaction can be appreciably accelerated by hot steam fixation (more than 100° C.) or warm fixation (50° to 60° C. in a sealed system), in which case it is complete after 1 to 2 hours and 12 to 24 hours respectively. The washout is reduced compared with known wood preservatives.

The pH of the aqueous impregnating solution is in general between pH 4 and pH 11, in particular between pH 6 and 9. Especially if the pH is set to below about pH 7.5 it is possible to incorporate into the concentrates and solutions even fungicides and insecticides which are not stable in an alkaline medium at a higher pH. Thus, to broaden the activity spectrum or to obtain particular effects it is also possible to use for example the following compounds with or without assistants such as ionic or nonionic emulsifiers and/or organic solvents:

Methylene bisthiocyanate
Chlorinated phenols
Tetrachloroisophthalodinitrile
N-Cyclohexyl-N-methoxy-2,5-dimethylfuran-3-carboxamide
N,N'-Dimethyl-N'-phenyl-(N-fluoromethylthio)sulfamide
N,N'-Dimethyl-N'-toluyl-(N-fluoromethylthio)sulfamide
Methyl benzimidazole-2-carbamate
2-Thiocyanomethylthiobenzothiazole
2-Iodobenzanilide
1-(1',2',4'-Triazol-1'-yl)-1-(4'-chlorophenoxy)-3,3-dimethylbutan-2-one
1-(1',2',4'-Triazol-1'-yl)-1-(4'-chlorophenoxy)-3,3-dimethylbutan-2-ol
Hexachlorocyclohexane
O,O-Diethyldithiophosphorylmethyl-6-chlorobenoxazolone
2-(1,3-Thiazol-4-yl)benzimidazole
N-Trichloromethylthio-3,6,7,8-tetrahydrophthalimide
N-(1,1,2,2-Tetrachloroethylthio)-3,6,7,8-tetrahydrophthalimide
N-Trichloromethylthiophthalimide
3-Iodo-2-propylbutyl carbamate
O,O-DimethylS-(2-methylamino-2-oxoethyl)dithiophosphate
O,O-Diethyl 0-(3,5,6-trichloro-2-pyridyl) thiophosphate
O,O-Dimethyl S-(N-phthalimido)methyl dithiophosphate
O,O-Diethyl 0-(α-cyanobenzylideneamino) thiophosphate
6,7,8,9,10-Hexachloro-1,5,5a,6,9,9a-hexahydro-6,9-methano-2,3,4-benzodioxothiepin 3-oxide
(4-Ethoxyphenyl)-(dimethyl)-(3-(4-fluoro-3-phenoxyphenyl)propylsilanes
2-sec-Butylphenyl N-methylcarbamate
2-Isopropoxyphenyl N-methylcarbamate
1-Naphthyl N-methylcarbamate
Norbornene dimethanohexachlorocyclosulfite
1-[4-Chlorophenyl]-3-(2,6-di-fluorobenzoyl)urea
Synthetic pyrethroids such as
3-Phenoxybenzyl (+)-3-(2,2-dichlorovinyl-2,2-dimethyl)cyclopropane-1-carboxylate
α-Cyano-3,3-phenoxybenzyl 3-(2,2-dichlorovinyl-2,2-dimethyl)cyclopropane-1-carboxylate
(S)-α-Cyano-3-phenoxybenzyl (1R,3R)-3-(2,2-dibromovinyl)-2,2-dimethylcyclopropanecarboxylate (deltamethrin)
α-Cyano-3-phenoxybenzylisopropyl 2,4-chlorophenylacetate.

The water-thinnable wood preservatives generally contain the copper and/or zinc and/or nickel and/or cobalt in concentrated form for example in an amount of from 1.0 to 12.5% by weight, calculated as metal.

Suitable concentrates have for example the following composition: (% by weight)

2.5–40% of copper and/or zinc and/or cobalt and/or nickel compounds
10–40% of a metal-fixing acid
5–50% of a complex polymeric nitrogen compound, pound, in particular polyethyleneimines,
0–25% of water-soluble amine and/or polyamine
0–40% of a compound having a fungicidally active anion
0–25% of N-organodiazeniumdioxy compounds
0–40% of a fatty amine and/or fatty amine salt or mixtures thereof
0–50% of a quaternary ammonium and/or quaternary phosphonium compound
0–20% of tridemorph, fenpropimorph, triazole and/or imidazole derivatives, tributyltin compounds and/or isothiazolone compounds and/or hydroxamic acids
0–2% of synthetic pyrethroids, the sum total being always 100% by weight, and optionally minor amounts of other constituents, such as ammonia, corrosion inhibitors, complexing acids (e.g. nitrilotriacetic acid, ethylenediaminetetraacetic acid if hard water is used) and if necessary water and/or polar water-miscible solvents, the proportion of which however can in general be kept to a minimum and which essentially aid handling.

However, the present invention equally extends to the less concentrated impregnating solutions preparable by dilution with water. The application concentration is for example from 0.01 to 1.50% by weight of metal, e.g. copper, in the aqueous impregnating solution, depending on the method of impregnation and the severity of hazard to which the impregnated wood will be exposed.

By dissolving the metal salts, if necessary by heating, in particular the copper and/or zinc compounds, in the polymeric complexing nitrogen compounds in the presence or absence of amines and water it is possible to prepare highly concentrated water-soluble pastes and liquids which on dilution with water can be used for impregnating wood.

The impregnating solutions can be applied to wood by hand, for example by spraying, brushing, dipping or trough impregnation, or by industrial methods, for example the pressure method, the changing pressure method or the double vacuum method. For the purposes of the present invention "wood" covers not only solid wood but also woodbase materials, for example chipboard or plywood; in this case the wood preservative may also be introduced with the glue.

The concentrates or solutions can be colored with water-soluble or water-emulsifiable dyes and/or pigment preparations. The addition of wax, paraffin and/or acrylate dispersions to obtain a water-repellent effect or improve the fixation is possible.

The concentrates may also be incorporated into binder-containing water-thinnable systems (primers, glazes).

The invention will be explained with reference to the following Examples:

| | |
|---|---|
| 20% | of aminoethylethanolamine |
| 25% | of 2-ethylhexanoic acid |
| 6% | of N-cyclohexyldiazeniumdioxy potassium (K-HDO)*) (hereinafter abbreviated to K-HDO) |
| 39% | of water |
| 10% | of copper hydroxide carbonate $Cu(OH)_2 \cdot CuCO_3$ |

The concentrate is diluted with water in a ratio of 2 parts of concentrate to 98 parts of water; that is, the application concentration is 2%.

In each Example, 20 pine sapwood blocks (15×25×50 mm) were impregnated, before 10 each of the impregnated blocks were subjected to
I: 4 weeks' affixation at standard temperature (20° C.) or
II: hot steam treament (1 h, 100° C.) and 4 hours' cooling down
and then repeatedly washed with water, the wash water being collected and its copper content being determined.

In the case of the hot steam treatment, the amount of copper in the condensed water (steam which had condensed at the surface of the blocks) was additionally analyzed and added to the copper content of the wash water to determine the total washout.

The amount of washed-out copper was calculated as a percentage of the total amount of copper in the wood prior to the washing out (no washout =0%, complete washout =100%).

| Copper washout | | |
|---|---|---|
| I | | 26% |
| II | a) | 9% (washout due to condensed water) |
| | b) | 21% (washout following hot steam treatment) |
| II | Total: | 30% |

Example B (not according to the invention)

| | |
|---|---|
| 15.0% | of diethylenetriamine |
| 25.0% | of 2-ethylhexanoic acid |
| 6.5% | of K-HDO |
| 43.5% | of water |
| 10.0% | of copper hydroxycarbonate $Cu(OH)_2 \cdot CuCO_3$ |

| Copper washout | | |
|---|---|---|
| I | | 31% |
| II | a) | 11% |
| | b) | 21% |
| II | Total: | 32% |

Example C (not according to the invention)

| | |
|---|---|
| 20% | of diethylenetriamine |
| 33% | of 2-ethylhexanoic acid |
| 34.5% | of water |
| 12.5% | of copper hydroxide carbonate |

| Copper washout | |
|---|---|
| I | 41.5% |

Example D (not according to the invention)

| | |
|---|---|
| 17.5% | of dipropylenetriamine |
| 25.0% | of 2-ethylexanoic acid |
| 6.0% | of K-HDO |
| 41.5% | of water |
| 10% | of copper hydroxycarbonate |

| Copper washout | | |
|---|---|---|
| I | | 21% |
| II | a) | 6% |
| | b) | 19% |
| | Total: | 25% |

To determine the penetration, 5 pinewood posts (1.50 m in length; 0.20 m in diameter; from the same growth area; in the air-dried state with comparatively narrow annual rings and an average sapwood width of above 3 cm) were each cut into 6 roundwood sections 24 cm in length and the cut surfaces were sealed off with a coat of epoxy resin. 1 section was taken from each post, so that 5 pine roundwood sections could be impregnated at the same time (1 h vacuum: less than 0.1 bar; 4 h pressure: 8 bar).

To determine the penetration of the copper the pine roundwood sections were then cut open in the middle and the cut surfaces were treated with 4-(2-pyridylazo)re sorcinol monosodium salt (monohydrate) (red color with copper and zinc) and the penetration of the copper was determined.

| Copper penetration (Series I/1) | | | | | | |
|---|---|---|---|---|---|---|
| | | a | b | c | d | e |
| average sapwood width (mm) | about | 35 | 33 | 38 | 30 | 42 |
| average copper penetration (mm) | about | 25 | 19 | 27 | 15 | 18 |

Example E (not according to the invention)

| | |
|---|---|
| 15.0% | of 1,3-diaminopropane |
| 25.0% | of 2-ethylhexanoic acid |
| 6.0% | of K-HDO |
| 44.0% | of water |
| 10.0% | of copper hydroxycarbonate $Cu(OH)_2 \cdot CuCO_3$ |

| Copper washout | | |
|---|---|---|
| I | | 18% |
| II | a) | 5% |
| | b) | 19% |
| Total: | | 24% |

| Copper penetration (Series I/2) | | | | | | |
|---|---|---|---|---|---|---|
| | | a | b | c | d | e |
| average sapwood width (mm) | about | 35 | 32 | 37 | 31 | 42 |
| average copper penetration (mm) | about | 22 | 19 | 26 | 15 | 19 |

EXAMPLES ACCORDING TO THE INVENTION

EXAMPLE 1

| | |
|---|---|
| 15% | of PEI ca. n = 150 |
| 9% | of aminoethylethanolamine |
| 23.5% | of 2-ethylhexanoic acid |
| 6.0% | of K-HDO |
| 36.5% | of water |
| 10.0% | of copper hydroxycarbonate |
| Application concentration: 2% | |

| Copper washout | | |
|---|---|---|
| I | | 6.5% |
| II | a) | 5.5% |
| | b) | 8.0% |
| Total: | | 13.5% |

| Copper penetration (Series I/3) | | | | | | |
|---|---|---|---|---|---|---|
| | | a | b | c | d | e |
| average sapwood width (mm) | about | 35 | 31 | 38 | 31 | 41 |
| average copper penetration (mm) | sapwood is fully penetrated; heartwood boundary is reached. | | | | | |

EXAMPLE 2

| | |
|---|---|
| 15% | of PEI ca. n = 150 |
| 6% | of diethylenetriamine |
| 22% | of isooctanoic acid |
| 6% | of K-HDO |
| 41% | of water |
| 10% | of copper hydroxycarbonate |
| Application concentration: 2% | |

| Copper washout | | |
|---|---|---|
| I | | 7.5% |
| II | a) | 5.0% |
| | b) | 8.5% |
| Total: | | 13.5% |

| Copper penetration (Series I/4) | | | | | | |
|---|---|---|---|---|---|---|
| | | a | b | c | d | e |
| average sapwood width (mm) | about | 37 | 34 | 36 | 33 | 40 |
| average copper penetration (mm) | sapwood is fully penetrated; heartwood boundary is reached. | | | | | |

EXAMPLE 3

| | |
|---|---|
| 14.5% | of PEI ca. n = 100 |
| 8.0% | of aminoethylethanolamine |
| 25.0% | of 2-ethylhexanoic acid |
| 6.5% | of K-HDO |
| 36.0% | of water |
| 10.0% | of copper hydroxycarbonate |
| Application concentration: 2% | |

| Copper washout | | |
|---|---|---|
| I | | 9.0% |
| II | a) | 7.0% |
| | b) | 5.5% |
| Total: | | 12.5% |
| III | | After fixation 12 hours at 60° C. in closed system: 10.5% |

| Copper penetration (Series I/5) | | | | | | |
|---|---|---|---|---|---|---|
| | | a | b | c | d | e |
| average sapwood width (mm) | about | 34 | 31 | 33 | 34 | 39 |
| average copper penetration (mm) | sapwood is fully penetrated; heartwood boundary is reached. | | | | | |

EXAMPLE 4

| | |
|---|---|
| 14.5% | of PEI ca. n = 100 |
| 9.0% | of aminoethylethanolamine |
| 23.5% | of isooctanoic acid |
| 36.5% | of water |
| 6.5% | of K-HDO |
| 10.0% | of copper hydroxycarbonate |
| Application concentration: 2% | |

| Copper washout | | |
|---|---|---|
| I | | 7.0% |
| II | a) | 5.0% |
| | b) | 7.5% |

-continued

| Copper washout | |
|---|---|
| Total: | 12.5% |

| Copper penetration (Series I/6) | | | | | | |
|---|---|---|---|---|---|---|
| | | a | b | c | d | e |
| average sapwood width (mm) | about | 36 | 32 | 36 | 33 | 49 |
| average copper penetration (mm) | sapwood is fully penetrated; heartwood boundary is reached. | | | | | |

EXAMPLE 5

| 14.5% | of PEI ca. n = 100 |
|---|---|
| 9.0% | of aminoethylethanolamine |
| 23.5% | of cyclohexanecarboxylic acid |
| 6.0% | of K-HDO |
| 37.0% | of water |
| 10.0% | of copper hydroxycarbonate |
| Application concentration: 2% | |

| Copper washout | | |
|---|---|---|
| I | | 10.0% |
| II | a) | 4.5% |
| | b) | 6.5% |
| Total: | | 11.0% |
| III | | 9.8% |

| Copper penetration (Series II/1) | | | | | | |
|---|---|---|---|---|---|---|
| | | a | b | c | d | e |
| average sapwood width (mm) | about | 47 | 30 | 31 | 35 | 42 |
| average copper penetration (mm) | sapwood is fully penetrated; heartwood boundary is reached. | | | | | |

EXAMPLE 6

| 15.0% | of PEI ca. n = 150 |
|---|---|
| 5.0% | of aminoethylethanolamine |
| 5.5% | of diethylenetriamine |
| 15.0% | of sebacic acid |
| 5.0% | of isononanoic acid |
| 6.0% | of K-HDO |
| 38.5% | of $H_2O$ |
| 10.0% | of copper hydroxycarbonate |
| Application concentration: 2% | |

| Copper washout | | |
|---|---|---|
| I | | 9.0% |
| II | a) | 5.0% |
| | b) | 7.0% |
| Total: | | 12.0% |

| Copper penetration (Series II/2) | | | | | | |
|---|---|---|---|---|---|---|
| | | a | b | c | d | e |
| average sapwood width (mm) | about | 46 | 31 | 30 | 36 | 44 |
| average copper penetration (mm) | sapwood is fully penetrated; heartwood boundary is reached. | | | | | |

EXAMPLE 7

| 14.5% | of PEI ca. n = 500 |
|---|---|
| 9.0% | of aminoethylethanolamine |
| 21.0% | of 2-ethylhexanoic acid |
| 4.0% | of phthalic anhydride |
| 6.0% | of K-HDO |
| 35.5% | of water |
| 10.0% | of copper hydroxycarbonate |
| Application concentration: 2% | |

| Copper washout | | |
|---|---|---|
| I | | 6.5% |
| II | a) | 4.0% |
| | b) | 5.5% |
| Total: | | 9.5% |

| Copper penetration (Series II/3) | | | | | | |
|---|---|---|---|---|---|---|
| | | a | b | c | d | e |
| average sapwood width (mm) | about | 46 | 31 | 33 | 36 | 41 |
| average copper penetration (mm) | sapwood is fully penetrated; heartwood boundary is reached. | | | | | |

EXAMPLE 8

| 14.5% | of PEI ca. n = 100 |
|---|---|
| 9.0% | of aminoethylethanolamine |
| 22.5% | of octanoic acid |
| 6.0% | of K-HDO |
| 38.0% | of water |
| 10.0% | of copper hydroxycarbonate |
| Application concentration: 2% | |

| Copper washout | | |
|---|---|---|
| I | | 7.0% |
| II | a) | 5.0% |
| | b) | 7.5% |
| Total: | | 12.5% |

| Copper penetration (Series II/4) | | | | | | |
|---|---|---|---|---|---|---|
| | | a | b | c | d | e |
| average sapwood width (mm) | about | 45 | 32 | 32 | 34 | 41 |
| average copper penetration (mm) | sapwood is fully penetrated; heartwood boundary is reached. | | | | | |

EXAMPLE 9

| | |
|---|---|
| 14.5% | of PEI ca. n = 150 |
| 9.0% | of aminoethylethanolamine |
| 27.0% | of $C_{10}$-Versatic acid |
| 6.0% | of K-HDO |
| 33.5% | of water |
| 10.0% | of copper hydroxycarbonate |

Application concentration: 2%

| Copper washout | | |
|---|---|---|
| I | | 6.5% |
| II | a) | 4.5% |
| | b) | 7.5% |
| Total: | | 12.0% |
| III | | 9.8% |

| Copper penetration (Series II/5) | | | | | | |
|---|---|---|---|---|---|---|
| | | a | b | c | d | e |
| average sapwood width (mm) | about | 48 | 33 | 32 | 34 | 43 |
| average copper penetration (mm) | sapwood is fully penetrated; heartwood boundary is reached. | | | | | |

EXAMPLE 10

| | |
|---|---|
| 15.0% | of PEI ca. n = 150 |
| 8.0% | of aminoethylethanolamine |
| 23.5% | of salicylic acid |
| 6.0% | of K-HDO |
| 37.5% | of water |
| 10.0% | of copper hydroxycarbonate |

Application concentration: 2%

| Copper washout | | |
|---|---|---|
| I | | 7.5% |
| II | a) | 4.0% |
| | b) | 8.0% |
| Total: | | 12.0% |
| III | | 9.5% |

| Copper penetration (Series II/6) | | | | | | |
|---|---|---|---|---|---|---|
| | | a | b | c | d | e |
| average sapwood width (mm) | about | 47 | 32 | 31 | 35 | 42 |
| average copper penetration (mm) | sapwood is fully penetrated; heartwood boundary is reached. | | | | | |

EXAMPLE 11

| | |
|---|---|
| 14.5% | of PEI ca. n = 150 |
| 8.0% | of aminoethylethanolamine |
| 26.0% | of 2-ethylhexanoic acid |
| 6.5% | of K-HDO |
| 37.6% | of water |
| 7.4% | of zinc oxide |

| Copper washout | |
|---|---|
| I | 10.0% |

| Copper penetration (Series II/1) | | |
|---|---|---|
| | a | b |
| average sapwood width (mm) | about 37 | 31 |
| average copper penetration (mm) | sapwood is fully penetrated; heartwood boundary is reached. | |

EXAMPLE 12

| | |
|---|---|
| 15.0% | of PEI ca. n = 150 |
| 9.0% | of aminoethylethanolamine |
| 23.5% | of isononanoic acid |
| 32.0% | of water |
| 4.0% | of boric acid |
| 6.5% | of K-HDO |
| 10.0% | of copper hydroxycarbonate |

Application concentration: 2%

| Copper washout | | |
|---|---|---|
| I | | 7.5% |
| II | a) | 6.0% |
| | b) | 8.0% |
| Total: | | 14.0% |

EXAMPLE 13

| | |
|---|---|
| 17.5% | of polymine ca. n = 150 |
| 5.0% | of dipropylenetriamine |
| 26.0% | of 2-ethylhexanoic acid |
| 21.5% | of water |
| 10.0% | of copper hydroxycarbonate |
| 4.0% | of propiconazole |
| 12.0% | of nonionic emulsifier (ethoxylated nonylphenol, about 9 ethylene oxide per phenol) |
| 4.0% | of propylene glycol |

Application concentration: 1.5%

| Copper washout | | |
|---|---|---|
| I | | 6.5% |
| II | a) | 4.0% |
| | b) | 6.0% |
| Total: | | 10.0% |

| Copper penetration | | |
|---|---|---|
| | a | b |
| average sapwood width (mm) | about 37 | 40 |
| average copper penetration (mm) | sapwood is fully penetrated; heartwood boundary is reached. | |

EXAMPLE 14

| | |
|---|---|
| 17.5% | of PEI ca. n = 500 |
| 5.0% | of dipropylenetriamine |

-continued

| | |
|---|---|
| 20.0% | of sorbic acid |
| 27.5% | of water |
| 10.0% | of copper hydroxycarbonate |
| 4.0% | of propiconazole |
| 12.0% | of nonionic emulsifier |
| 4.0% | of propylene glycol |
| Application concentration: 1.5% | |

| Copper washout | |
|---|---|
| I | 8.5% |

EXAMPLE 15

| | |
|---|---|
| 17.5% | of PEI ca. n = 150 |
| 5.0% | of dipropylenetriamine |
| 18.0% | of sebacic acid |
| 29.5% | of water |
| 10.0% | of copper hydroxycarbonate |
| 4.0% | of propiconazole |
| 12.0% | of nonionic emulsifier |
| 4.0% | of propylene glycol |
| Application concentration: 1.5% | |

| Copper washout | | |
|---|---|---|
| I | | 5.3% |
| II | a) | 3.2% |
| | b) | 4.6% |
| Total: | | 7.8% |

EXAMPLE 16

| | |
|---|---|
| 14.5% | of PEI ca. n = 150 |
| 4.2% | of dipropylenetriamine |
| 22.5% | of isononanoic acid |
| 27.0% | of benzalconium chloride ($C_{12}$–$C_{14}$) (N-$C_{12}$-$C_{14}$-alkyl, N-benzyl, N,N-dimethyl-ammonium chloride) |
| 8.3% | of copper hydroxycarbonate |
| 23.5% | of water |
| Application concentration: 2% | |

| Copper washout | |
|---|---|
| I | 10.0% |

| Copper penetration | | a | b |
|---|---|---|---|
| average sapwood width (mm) | about | 32 | 41 |
| average copper penetration (mm) | sapwood is fully penetrated; heartwood boundary is reached. | | |

EXAMPLE 17

| | |
|---|---|
| 8.0% | of PEI ca. n = 150 |
| 13.5% | of isononanoic acid |
| 8.5% | of dipropylenetriamine |
| 25.0% | of boric acid |
| 16.0% | of benzalconium chloride |
| 24.0% | of water |
| 5.0% | of copper hydroxycarbonate |
| Application concentration: 2% | |

| Copper washout | | |
|---|---|---|
| I | | 10.0% |
| II | a) | 4.0% |
| | b) | 6.0% |
| Total: | | 10.0% |

| Copper penetration | | a | b |
|---|---|---|---|
| average sapwood width (mm) | about | 42 | 31 |
| average copper penetration (mm) | sapwood is fully penetrated; heartwood boundary is reached. | | |

EXAMPLE 18

| | |
|---|---|
| 8.0% | of PEI ca. n = 150 |
| 5.0% | of dipropylenetriamine |
| 26.0% | of 2-ethylhexanoic acid |
| 21.5% | of water |
| 10.0% | of copper hydroxycarbonate |
| 3.0% | of TBT benzoate |
| 14.0% | of nonionic emulsifier |
| 3.0% | of propylene glycol |
| Application concentration: 2% | |

| Copper washout | | |
|---|---|---|
| I | | 7.5% |
| II | a) | 5.0% |
| | b) | 6.5% |
| Total: | | 11.5% |

| Copper penetration | | a | b |
|---|---|---|---|
| average sapwood width (mm) | about | 31 | 34 |
| average copper penetration (mm) | sapwood is fully penetrated; heartwood boundary is reached. | | |

EXAMPLE 19

| | |
|---|---|
| 14.5% | of PEI ca. n = 150 |
| 8.0% | of aminoethylethanolamine |
| 25.0% | of 2-ethylhexanoic acid |
| 10.0% | of benzisothiazolone, sodium salt |
| 32.5% | of water |
| 10.0% | of copper hydroxycarbonate |
| Application concentration: 2% | |

| Copper washout | | |
|---|---|---|
| I | | 6.5% |
| II | a) | 5.0% |
| | b) | 3.0% |
| Total: | | 8.0% |

EXAMPLE 20

| | |
|---|---|
| 15.0% | of polymine ca. n = 500 |
| 8.0% | of aminoethylethanolamine |
| 22.0% | of 2-ethylhexanoic acid |
| 6.0% | of 2-mercaptopyridine N-oxide |
| 39.0% | of water |
| 10.0% | of copper hydroxycarbonate |

Application concentration: 2%

| Copper washout | | |
|---|---|---|
| I | | 9.5% |
| II | a) | 6.5% |
| | b) | 5.5% |
| | Total: | 12.0% |

EXAMPLE 21

| | |
|---|---|
| 15.0% | of PEI ca. n = 150 |
| 9.0% | of aminoethylethanolamine |
| 20.0% | of 2-ethylhexanoic acid |
| 10.0% | of 2-hydroxypyridine N-oxide |
| 36.0% | of water |
| 10.0% | of copper hydroxycarbonate |

Application concentration: 2%

| Copper washout | | |
|---|---|---|
| I | | 8.5% |
| II | a) | 5.0% |
| | b) | 7.5% |
| | Total: | 12.5% |

EXAMPLE 22

| | |
|---|---|
| 14.5% | of PEI ca. n = 500 |
| 10.0% | of aminoethylethanolamine |
| 20.0% | of 2-hydroxypyridine N-oxide |
| 6.0% | of K-HDO |
| 29.5% | of water |
| 10.0% | of copper hydroxycarbonate |

Application concentration: 2%

| Copper washout | | |
|---|---|---|
| I | | 9.0% |
| II | a) | 7.0% |
| | b) | 5.5% |
| | Total: | 12.5% |

EXAMPLE 23

| | |
|---|---|
| 14.5% | of PEI ca. n = 500 |
| 21.5% | of isooctanoic acid |
| 7.5% | of copper hydroxide |
| 35.0% | of benzalconium chloride ($C_{12}/C_{14}$) |
| 21.5% | of water |

Application concentration: 2%

| Copper washout | |
|---|---|
| I | 10.5% |

| Copper washout | | |
|---|---|---|
| II | a) | 6.5% |
| | b) | 7.0% |
| | Total: | 13.5% |

| Copper penetration | | |
|---|---|---|
| | a | b |
| average sapwood width (mm) | about 33 | 37 |
| average copper penetration (mm) | sapwood is fully penetrated; heartwood boundary is reached. | |

EXAMPLE 24

| | |
|---|---|
| 13.50% | of PEI ca. n = 500 |
| 25.75% | of 2-ethylhexanoic acid |
| 7.00% | of copper hydroxide |
| 11.50% | of dimethylalkylamine ($C_{12}/C_{14}$) (N-$C_{12}$-$C_{14}$-alkyl, N,N-dimethylamine) |
| 7.50% | of tridemorph |
| 9.75% | of ethoxylated coco fatty amine (density 0.96 g/cm$^3$ at 50° C.) |
| 25.00% | of water |

Application concentration: 2%

| Copper washout | | |
|---|---|---|
| I | | 5.5% |
| II | a) | 3.5% |
| | b) | 3.5% |
| | Total: | 7.0% |

EXAMPLE 25

| | |
|---|---|
| 11.75% | of PEI ca. n = 130 |
| 3.25% | of dipropylenetriamine |
| 22.33% | of 2-ethylhexanoic acid |
| 29.33% | of water |
| 6.67% | of copper hydroxycarbonate |
| 10.00% | of dimethylalkylamine ($C_{12}/C_{14}$) |
| 6.67% | of tridemorph |
| 10.00% | of ethoxylated coco fatty amine (density 0.96 g/cm$^3$ at 50° C.) |

Application concentration: 1.5%

| Copper washout | | |
|---|---|---|
| I | | 7.0% |
| II | a) | 5.0% |
| | b) | 4.0% |
| | Total: | 9.0% |

| Copper penetration | | |
|---|---|---|
| | a | b |
| average sapwood width (mm) | about 36 | 30 |
| average copper penetration (mm) | sapwood is fully penetrated; heartwood boundary is reached. | |

EXAMPLE 26

| | |
|---|---|
| 14.50% | of PEI ca. n = 150 |
| 8.00% | of aminoethylethanolamine |
| 25.50% | of 2-ethylhexanoic acid |
| 4.50% | of K-HDOr |
| 37.35% | of water |
| 10.00% | of copper hydroxycarbonate |
| 0.15% | of deltamethrin |

| Copper washout | | |
|---|---|---|
| I | | 6.5% |
| II | a) | 3.5% |
| | b) | 4.0% |
| Total: | | 8.5% |

EXAMPLE 27

| | |
|---|---|
| 27.00% | of PEI ca. n = 500 |
| 33.00% | of 2-ethylhexanoic acid |
| 28.75% | of water |
| 11.25% | of copper hydroxide |
| Application concentration: 2% | |

| Copper washout | | |
|---|---|---|
| I | | 11.0% |
| II | a) | 6.0% |
| | b) | 6.5% |
| Total: | | 12.5% |

| | Copper penetration | |
|---|---|---|
| | a | b |
| average sapwood width (mm) | about 36 | 32 |
| average copper penetration (mm) | sapwood is fully penetrated; heartwood boundary is reached. | |

EXAMPLE 28

| | |
|---|---|
| 14.5% | of PEI ca. n = 500 |
| 7.0% | of aminoethylethanolamine |
| 26.0% | of 2-ethylhexanoic acid |
| 4.0% | of N-cyclohexyl-2,5-dimethylfuran-3-hydroxamic acid, sodium salt |
| 38.5% | of water |
| 10.0% | of copper hydroxycarbonate |
| Application concentration: 2% | |

| Copper washout | | |
|---|---|---|
| I | | 8.5% |
| II | a) | 5.0% |
| | b) | 5.0% |
| Total: | | 10.0% |

What is claimed is:

1. A water-soluble wood preservative comprising:
   (a) a wood-preserving effective mount of a metal compound selected from the group consisting of copper compounds, zinc compounds and a mixture thereof;
   (b) a metal-fixing acid selected from the group consisting of aliphatic $C_{5-20}$-carboxylic acids, halogen substituted $C_{5-20}$-carboxylic acids, amino substituted $C_{5-20}$-carboxylic acids, alkoxy substituted $C_{5-20}$-carboxylic acids, aliphatic $C_{5-20}$-dicarboxylic acids aminohydroxy $C_{5-20}$-carboxylic acids, 2-mercaptopyridine C-oxide, 2-hydroxypyridine N-oxide, dehydroacetic acid, cycloalkyl carboxylic acids, aryl carboxylic acids, polycarboxylic acids, and heterocyclic carboxylic acids; and
   (c) a washout-reducing effective amount of a polyethyleneimine having a degree of polymerization between 50 and 1000.

2. The water-soluble wood preservative of claim 1, further comprising a water-soluble amine selected from the group consisting of aliphatic linear polyamines, aliphatic branched polyamines, alkanolamines, diamines of cyclic compounds, polyamines of cyclic compounds and ammonia.

3. The water-soluble wood preservative of claim 1, wherein said metal compound is present in from 2.5–40 wt. %.

4. The water-soluble with wood preservative of claim 1, wherein said metal-fixing acid is present in from 10–40 wt. %.

5. The water-soluble wood preservatives of claim 1, wherein said polyethyleneimine is present in from 5–50 wt. %.

6. The water-soluble wood preservative of claim 1, further comprising an additive selected from the group consisting of fungicidally active anions, N-organodiazeniumdioxy compounds, fatty amines, fatty amine salts, quaternary ammonium compounds, quaternary phosphonium compounds, tridemorph derivatives, fenpropimorph derivatives, triazole derivatives, imidazole derivatives, tributyl tin compounds, isothiazolone compounds, hydroxamic acids, and synthetic pyrethroids or a mixture thereof.

7. The water-soluble wood preservatives of claim 1, wherein said metal-fixing acid is 2-ethylhexanoic acid.

8. A process for protecting wood, which comprises treating wood with an effective wood protecting amount of a preservative as claimed in claim 1.

* * * * *